(12) United States Patent
Emtell

(10) Patent No.: US 6,718,978 B2
(45) Date of Patent: Apr. 13, 2004

(54) MANUAL VENTILATION BAG

(75) Inventor: Pär Emtell, Vällingby (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 10/040,880

(22) Filed: Jan. 7, 2002

(65) Prior Publication Data
US 2002/0104538 A1 Aug. 8, 2002

(30) Foreign Application Priority Data
Jan. 10, 2001 (SE) .............................. 0100066

(51) Int. Cl.[7] .............................. A61M 16/00
(52) U.S. Cl. .............................. 128/204.28; 128/205.13; 128/205.17

(58) Field of Search ................ 128/200.24, 203.12, 128/203.28, 204.18, 204.28, 205.13–205.17, 205.24, 205.25, 203.14–207.18

(56) References Cited
U.S. PATENT DOCUMENTS

| | | |
|---|---|---|
| 2,103,144 A | 12/1937 | Carre |
| 3,291,121 A | 12/1966 | Vizneau |
| 4,543,951 A | 10/1985 | Phuc |
| 4,821,712 A * | 4/1989 | Gossett .................. 128/205.15 |
| 4,883,051 A * | 11/1989 | Westenskow et al. .. 128/204.21 |

* cited by examiner

Primary Examiner—Glenn K. Dawson

(57) ABSTRACT

A manual ventilation bag has a first opening and a second opening, a first soft bag connected to the first opening and a second soft bag connected to the second opening. The manual ventilation bag is advantageously used in combination with a breathing apparatus.

6 Claims, 2 Drawing Sheets

MANUAL VENTILATION BAG

BACKGROUND OF THE INVENTION

1. Field of the Invention

The present invention relates to a manual ventilation bag and to a breathing apparatus employing a manual ventilation bag.

2. Description of the Prior Art

Manual ventilation bags are customarily used by a physician for controlling or supporting a patient's breathing. The physician squeezes the bag to press gas toward the patient and releases the bag to permit an exhalation. There are two basic forms of bags, having very different characteristics. One is the hard bag, which is made to re-inflate itself whenever squeezed. The other is the soft bag, which adapts to the flows and pressures within the system and provided by the operator. The present invention relates to ventilation bags of the soft kind.

When the physician operates the soft manual ventilation bag, he or she is able to feel the patient's lungs (resistance and compliance). This is an outstanding advantage in comparison to the hard bags. One disadvantage of this procedure (with soft bags) is that exhaled gas goes into the bag and to a certain degree is returned right back to the patient's lungs at the following inspiration.

Manual ventilation with soft bags is therefore usually employed with a breathing apparatus generating a constant flow of fresh gas flowing in hoses past the patient. The flow of fresh gas is mixed with the exhaled gas and fills the bag. This reduces re-breathing but is insufficient in many instances.

Periodic replacement of the gas in the manual ventilation bag is one way to reduce re-breathing further, but this causes a brief interruption in the patient's treatment.

The hard, self-inflating bag does not have this problem. It usually has a valve at each end and is filled through the valve with fresh breathing gas (usually air). Another way is to use coaxial connections, as shown in U.S. Pat. No. 3,291,121. However, as stated above, one common, major disadvantage of all hard bags is the physician's loss of an ability to feel the lungs. Another disadvantage is the increased number of valves required for the operation of the hard bag. These valves impede flow.

One known way to avoid re-breathing with soft bags is to force expired gas away from the bag during patient exhalation at the same time as fresh breathing gas fills the bag in the exact same way expired gas would have done. In this procedure, the physician is still able to feel the lungs, and only fresh breathing gas fills the bag. This procedure works excellently but requires the use of flow or pressure sensors and relatively rapid control of the valves in the breathing apparatus for evacuating expired gas and admitting fresh breathing gas.

There is a demand and need for a soft manual ventilation bag with the same function as the latter procedure but which is simpler to use in any situation, even when no electricity is available (not even batteries).

SUMMARY OF THE INVENTION

An object of the present invention is to provide a soft manual ventilation bag which is simple and easy to use in any situation requiring manual ventilation.

Another object of the invention is to provide a breathing apparatus with a manual ventilation capability.

The first objective is achieved according to the invention in a manual ventilation bag wherein two separate soft bags are combined as to form one manual ventilation bag with two openings allow simple separation of gas flows to and from the patient with no loss of the feeling of the lungs for the operator. The openings to which the soft bags are connected can be arranged side by side, coaxial or in any other suitable arrangement.

When the openings are coaxially arranged, one soft bag is suitably arranged inside the other soft bag. The soft bags can be protected by a soft cover. The soft cover is preferably transparent (as may the other soft bag be in the coaxial arrangement).

The second object is achieved according to the invention in a breathing apparatus having a manual ventilation bag as described above.

The breathing apparatus has several advantages due to the design with two separate soft bags.

The breathing apparatus can be e.g. a ventilator with an inspiratory line and an expiratory line. The inspiratory line is connected to one of the soft bags, and the expiratory line is connected to the other soft bag. To a physician using the manual ventilation bag, inhalations and exhalations will, in principle, feel the same as with a manual single-bag ventilation bag. However, there will be a major difference for the patient, since fresh breathing gas is always supplied for inhalations.

DESCRIPTION OF THE PREFERRED EMBODIMENTS

Figure 1:
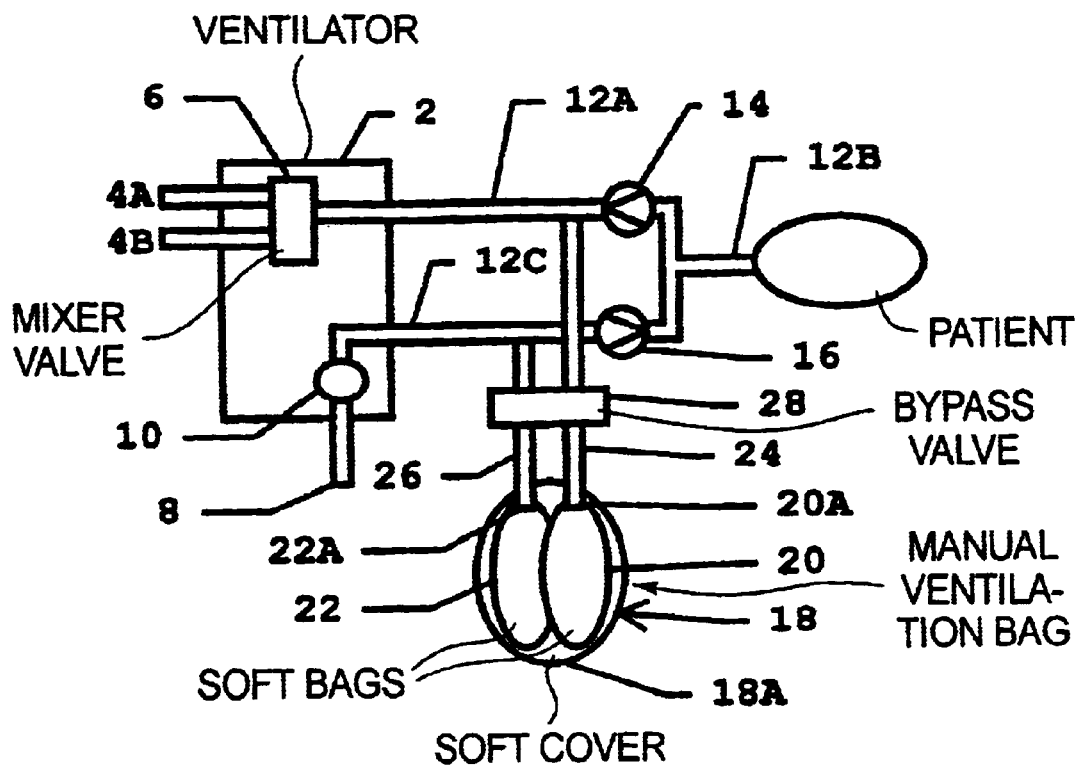
FIG. 1 illustrates a first embodiment of the manual ventilation bag and breathing apparatus according to the invention.

FIG. 1 shows a conventional ventilator 2, which could be a Servo Ventilator 300 or Servo Ventilator 900 (Siemens-Elema AB, Solna, Sweden). A detailed explanation of the ventilator 2 is not necessary, but gas connections 4A, 4B for the gases constituting the breathing gas (e.g. air and oxygen), a gas mixer 6 which proportions, mixes and regulates the connected gases into a specific flow of breathing gas, an outlet 8 and a valve 10 for exhaled breathing gas are schematically depicted.

An inspiratory line 12A carries the breathing gas from the ventilator 2 to a patient line 12B. The patient line 12B can be any conventional patient connection, e.g. a tracheal tube, facemask or tracheostomy tube.

Exhaled gas is carried in the patient line 12B from the patient to an expiratory line 12C connected to the ventilator 2.

A first check valve 14 can be arranged in the inspiratory line 12A, and a second check valve 16 can be arranged in the expiratory line 12C. The check valves 14,16 ensure that breathing gas only flows in one direction through the inspiratory line 12A and the expiratory line 12C. The check valves 14,16 are not essential and can be omitted.

A manual ventilation bag 18 according to the invention is also shown in FIG. 1. The manual ventilation bag 18 has a soft cover 18A in which a first soft bag 20 and a second soft bag 22 are arranged. The first soft bag 20 is connected, via a first opening 20A and a first line 24, to the inspiratory line 12A, upstream from the first check valve 14. The second soft bag 22 is connected, via a second opening 22A and a second line 26, to the expiratory line 12C, downstream from the second check valve 16.

In manual ventilation, the ventilator 2 normally delivers a constant flow of breathing gas into the inspiratory line 12A. This constant stream of breathing gas flows past the patient line 12B and passes through the expiratory valve 12C to the outlet 8.

When the physician squeezes the soft cover 18A, gas is forced out of the first soft bag 20, through the first line 24 to the inspiratory line 12A. Since this injection of gas increases pressure in the inspiratory line 12A, a flow of gas is generated through the patient line 12B to the patient. This flow is mainly governed by the way in which the physician squeezes the cover 18A. The physician accordingly has complete control over the patient's inhalation.

At the same time, gas in the second soft bag 22 is forced out into the expiratory line 12C and through the valve 10 to the outlet 8. Thus, the second soft bag 22 is also emptied during the inhalation phase.

When the physician decides exhalation should begin, she/he relaxes pressure on the cover 18A. This can be performed slowly or rapidly, depending on how the physician wants exhalation to proceed.

The physician's release of pressure on the cover 18A allows fresh breathing gas to flow down into the first soft bag 20. The second soft bag 22 is simultaneously filled with exhaled breathing gas from the patient. Since the flow of fresh breathing gas is constant, in principle, the physician's ability to feel the patient's lungs during exhalation is not affected. Excess gas flows out through the outlet 8. A new inhalation can then follow.

The effect of the above-described procedure can be enhanced and the physician's feel improved if the soft bags 20, 22 and the cover 18A are devised to enable the physician to squeeze and release each soft bag 20, 22 individually. The physician can then e.g. empty the second soft bag 22 during the final phase of inhalation and then wait to fill the first soft bag 20 until the end of exhalation.

The manual ventilation bag 18 can be disconnected from the lines 12A, 12C with a bypass valve 28.

Figure 2:
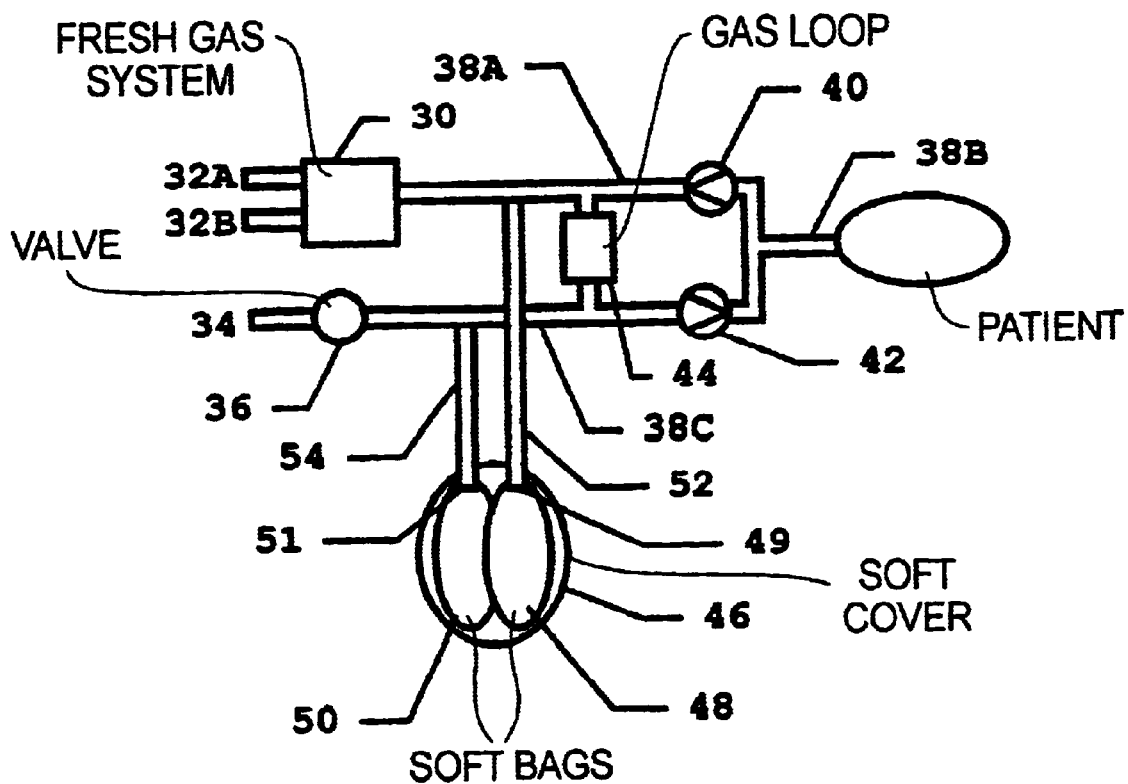
FIG. 2 illustrates a second embodiment of the manual ventilation bag and breathing apparatus according to the invention.

A second embodiment is shown in FIG. 2. A conventional fresh gas system 30 for anaesthesia mixes and regulates input gases from gas inlets 32A, 32B. In this embodiment, even anaesthetic is added to the breathing gas in the fresh gas system 30. It is not necessary to show this because it is well known and the preparation of fresh gas is not relevant to the invention. Any means for providing the anaesthetic is combinable with the manual ventilation bag according to the invention—even supplying the anaesthetic directly into one of the soft bags.

An outlet 34 discharges excess gas through a valve 36, e.g. a pressure relief valve, but the valve can also be an electronic valve or some other kind of valve.

An inspiratory line 38A carries breathing gas to a patient line 38B. The patient line 38B is connected, in turn, to an expiratory valve 38C. A first check valve 40 can be arranged in the inspiratory line 38A, and a second check valve 42 can be arranged in the expiratory line 38C so gas only passes in one direction.

Expired breathing gas is re-used after carbon dioxide is removed in a gas loop 44.

In principle, the part of the inspiratory line 38A upstream from the gas loop 44 is usually referred to, in principle, as the fresh gas line. The part of the inspiratory line 38A downstream from the gas loop 44, plus the patient line 38B, the expiratory line 38C and the gas loop 44, is usually referred to as the breathing circle.

A manual ventilation bag is connected to the inspiratory line 38A and the expiratory line 38C.

As in the above, the manual ventilation bag has a soft cover 46 in which a first soft bag 48 and a second soft bag 50 are arranged. The first soft bag 48 is connected to the inspiratory line 38A via a first opening 49 and a first line 52, and the second soft bag 50 is connected to the expiratory line 38C via a second opening 51 and a second line 54.

When the physician compresses the manual ventilator bag for an inhalation, gas flows from the first soft bag 48 up to the inspiratory line 38A and on to the patient via the patient line 38B. At the same time, gas flows from the second soft bag 50 to the expiratory line 38C and, via the gas loop 44, up to the inspiratory line 38A and on to the patient via the patient line 38B.

When the physician releases pressure on the manual ventilation bag during exhalation, fresh breathing gas flows down into the first soft bag 48 from the inspiratory line 38A. At the same time, expired breathing gas flows down into the second soft bag 50. In the final phase of exhalation, when the second soft bag 50 has been filled, excess gas will flow out to the outlet 34 through the pressure relief valve 36.

As in the preceding example, the manual ventilation bag can be devised to enable the physician to press and release either of the soft bags 48, 50 as desired. This allows the physician to have a direct impact on the extent to which expired gas is re-used.

With different resistances for flow between the soft bags and between the soft bags and the patient line, the flow of gases can be influenced in the required manner (e.g. causing fresh gas, and not expired gas, to fill the soft bag at the inspiratory line). The resistance can be incorporated with existing check valves, additional check valves (e.g. in the inspiratory line 38A between the line 52 and the gas loop 44) or with chokes.

Figure 3:
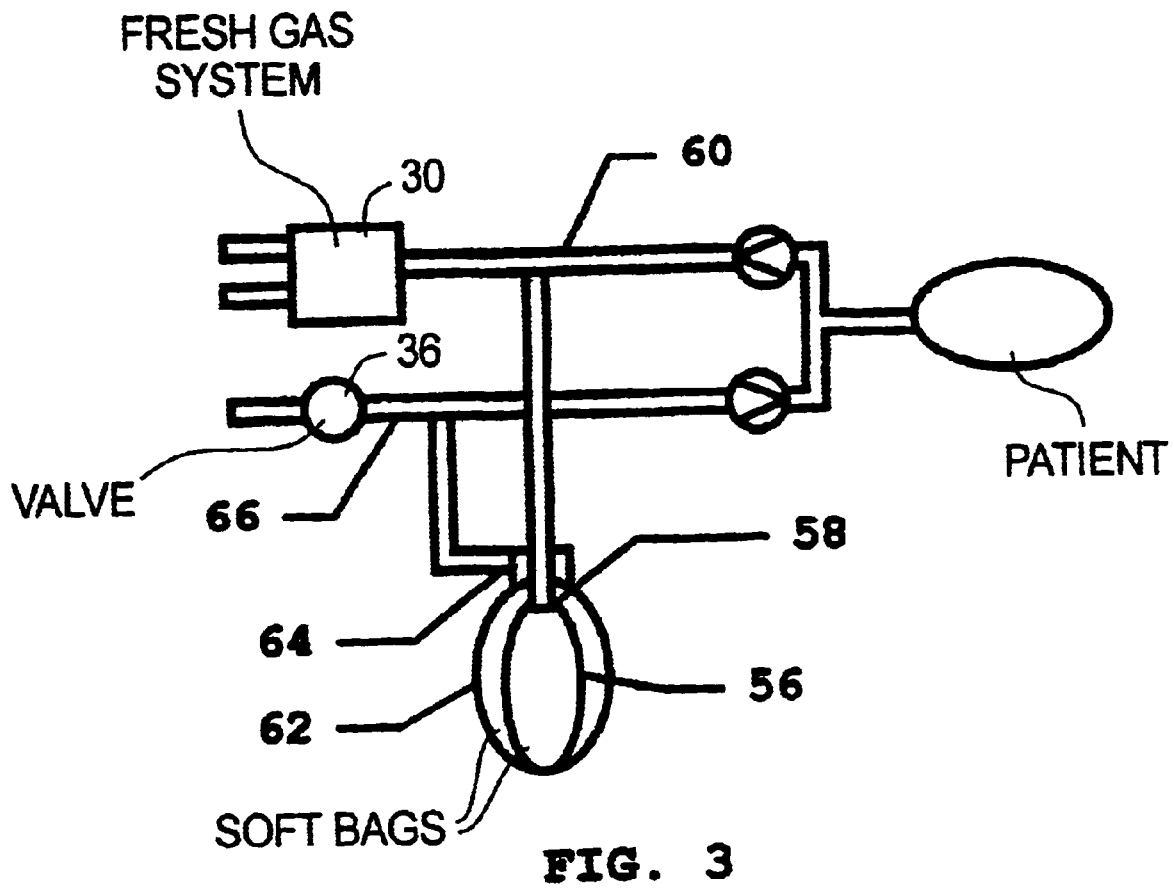
FIG. 3 illustrates a third embodiment of the manual ventilation bag according to the invention.

In FIG. 3 a third embodiment of the manual ventilation bag is shown. A first soft bag 56 is connected to a first opening 58. The first opening 58, in use with a breathing apparatus, can be connected to an inspiratory line 60. A second soft bag 62 is arranged around the first soft bag 56 and is connected to a second opening 64, which is coaxial in relation to the first opening 58. The second opening in use can be connected to an expiratory line 66.

Since the first soft bag 56 is arranged within the second soft bag 62, there is no need for a separate cover. The second soft bag 62 could preferably be transparent, so the first soft bag 56 is readily visible.

In contrast to similar arrangements with hard bags, the two soft bags 56, 62 can be more easily controlled and even separately compressed by the user, especially since the first soft bag 56 can be partially attached to the inside of the second soft bag 62.

Figure 4:
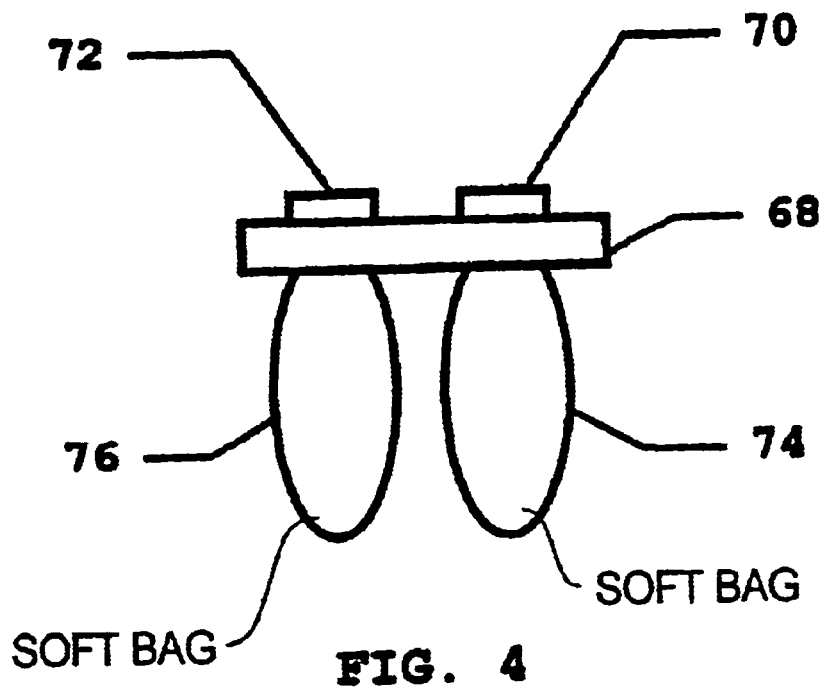
FIG. 4 illustrates a fourth embodiment of the manual ventilation bag.

In FIG. 4 a fourth embodiment of a manual ventilation bag according to the invention is shown. In a holder 68 a first opening 70 and a second opening 72 are arranged, connectable via tubes (not shown) to a breathing apparatus. A first soft bag is connected to the first opening 70 in the holder 68 and a second soft bag is connected to the second opening 72 in the holder 68.

The combination of a breathing apparatus and manual ventilation bag is not limited to the described embodiments. The manual ventilation bag according to the invention can be combined with all known breathing apparatuses with which manual ventilation is an option. The breathing apparatus can naturally include all known accessories that are suitable for use with these apparatuses, such as bacteria filter, heat-moist exchanger, humidifier, dehumidifier, water trap, etc.

Although modifications and changes may be suggested by those skilled in the art, it is the intention of the inventor to embody within the patent warranted hereon all changes and modifications as reasonably and properly come within the scope of his contribution to the art.

I claim as my invention:

1. A soft manual ventilation bag comprising a first opening, a second opening, a first soft bag connected to said first opening, and a second soft bag connected to said second opening and a soft cover containing said first soft bag and said second soft bag.

2. A breathing apparatus comprising:
 a breathing assist device adapted for interacting with a patient having an inspiration gas line and an expiration gas line; and
 a soft manual ventilation bag having a first opening connected to said inspiration gas line and a second opening connected to said expiration gas line, a first soft bag connected to said first opening, and a second soft bag connected to said second opening.

3. A breathing apparatus as claimed in claim 2 wherein said first opening and said second opening are disposed coaxially relative to each other.

4. A breathing apparatus as claimed in claim 3 wherein said first soft bag is disposed inside said second soft bag.

5. A breathing apparatus as claimed in claim 2 comprising a soft cover containing said first soft bag and said second soft bag.

6. A breathing apparatus as claimed in claim 5 wherein said breathing assist device is an anaesthetic delivery apparatus, and wherein said expiration line is a part of a breathing circuit adapted for circulating breathing gas to and from a patient, and wherein said inspiration line is a fresh gas line for supplying fresh breathing gas to said breathing circuit.

* * * * *